(12) United States Patent
Ortiz et al.

(10) Patent No.: US 7,404,509 B2
(45) Date of Patent: *Jul. 29, 2008

(54) ELECTROACTIVE POLYMER-BASED ARTICULATION MECHANISM FOR LINEAR STAPLER

(75) Inventors: Mark Ortiz, Milford, OH (US); Frederick Shelton, IV, Hillsboro, OH (US); Jeffrey Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 286 days.

This patent is subject to a terminal disclaimer.

(21) Appl. No.: 11/162,986

(22) Filed: Sep. 30, 2005

(65) Prior Publication Data

US 2006/0025817 A1 Feb. 2, 2006

Related U.S. Application Data

(63) Continuation-in-part of application No. 11/082,495, filed on Mar. 17, 2005.

(60) Provisional application No. 60/591,694, filed on Jul. 28, 2004.

(51) Int. Cl.
*A61B 17/068* (2006.01)

(52) U.S. Cl. .................. 227/176.1; 227/19; 227/175.1; 227/180.1; 606/139; 606/219

(58) Field of Classification Search ............ 227/19, 227/176.1, 178.1, 180.1, 175.1; 606/139, 606/219, 142, 34, 39

See application file for complete search history.

(56) References Cited

U.S. PATENT DOCUMENTS

| 5,290,240 | A | * | 3/1994 | Horres, Jr. | .................. 604/31 |
| 5,441,193 | A | | 8/1995 | Gravener | |
| 5,465,895 | A | | 11/1995 | Knodel et al. | |
| 5,503,638 | A | | 4/1996 | Cooper et al. | |
| 5,542,594 | A | | 8/1996 | McKean et al. | |
| 5,549,628 | A | | 8/1996 | Cooper et al. | |
| 5,599,329 | A | * | 2/1997 | Gabbay | .................. 604/284 |
| 5,673,840 | A | | 10/1997 | Schulze et al. | |
| 5,673,841 | A | | 10/1997 | Schulze et al. | |
| 5,702,409 | A | | 12/1997 | Rayburn et al. | |
| 5,769,892 | A | | 6/1998 | Kingwell | |

(Continued)

FOREIGN PATENT DOCUMENTS

EP      0 832 605 A      4/1998

(Continued)

*Primary Examiner*—Scott A. Smith
(74) *Attorney, Agent, or Firm*—Nutter McClennen & Fish LLP

(57) ABSTRACT

Methods and devices are provided for actuating and/or articulating a surgical stapler. In one embodiment, a surgical stapler is provided having a stapling mechanism or end effector that is movably coupled to a distal end of an elongate shaft. An electrically expandable and contractible actuator, such as an electroactive polymer actuator, can be used to pivotally or angularly adjust a position of the stapling mechanism relative to the elongate shaft by delivering energy to the electroactive polymer actuator. In another embodiment, an electroactive polymer actuator can be used to actuate the staple applying assembly, thereby driving one or more staples, and preferably at least two linear rows of staples, into tissue. The actuator can alternatively or additionally drive a blade distally to cut tissue being stapled.

22 Claims, 14 Drawing Sheets

U.S. PATENT DOCUMENTS

| | | | |
|---|---|---|---|
| 5,797,537 | A | 8/1998 | Oberlin et al. |
| 5,810,855 | A | 9/1998 | Rayburn et al. |
| 5,855,565 | A * | 1/1999 | Bar-Cohen et al. ......... 604/104 |
| 5,865,361 | A | 2/1999 | Milliman et al. |
| 5,902,312 | A | 5/1999 | Frater et al. |
| 5,908,427 | A | 6/1999 | McKean et al. |
| 5,964,774 | A | 10/1999 | McKean et al. |
| 6,063,097 | A | 5/2000 | Oi et al. |
| 6,503,257 | B2 | 1/2003 | Grant et al. |
| 6,656,193 | B2 | 12/2003 | Grant et al. |
| 6,667,825 | B2 | 12/2003 | Lu et al. |
| 6,740,079 | B1 * | 5/2004 | Eggers et al. ................. 606/34 |
| 6,835,173 | B2 | 12/2004 | Couvillon, Jr. |
| 6,923,804 | B2 * | 8/2005 | Eggers et al. ................. 606/34 |
| 6,969,395 | B2 * | 11/2005 | Eskuri ........................ 606/200 |
| 7,140,528 | B2 * | 11/2006 | Shelton, IV ............. 277/175.4 |
| 7,143,925 | B2 * | 12/2006 | Shelton et al. .......... 227/175.2 |
| 7,147,138 | B2 * | 12/2006 | Shelton, IV ............. 227/176.1 |
| 7,208,005 | B2 | 4/2007 | Frecker et al. |
| 7,213,736 | B2 * | 5/2007 | Wales et al. .............. 227/180.1 |
| 2003/0065358 | A1 | 4/2003 | Frecker et al. |
| 2003/0069474 | A1 | 4/2003 | Couvillon |
| 2004/0097971 | A1 | 5/2004 | Hughett |
| 2005/0006434 | A1 | 1/2005 | Wales et al. |
| 2005/0165415 | A1 | 7/2005 | Wales |
| 2005/0173490 | A1 | 8/2005 | Shelton |
| 2005/0067457 | A1 | 11/2005 | Shelton et al. |
| 2004/0232197 | A1 | 12/2005 | Shelton et al. |
| 2004/0232196 | A1 | 2/2006 | Shelton et al. |
| 2005/0067458 | A1 | 2/2006 | Swayze et al. |

FOREIGN PATENT DOCUMENTS

| | | |
|---|---|---|
| EP | 1 323 384 A | 7/2003 |
| EP | 1 522 264 A | 4/2005 |
| WO | WO 99/02090 | 1/1999 |
| WO | WO 03/094743 | 11/2003 |
| WO | WO 2004/050971 | 6/2004 |

* cited by examiner

ELECTROACTIVE POLYMER-BASED ARTICULATION MECHANISM FOR LINEAR STAPLER

CROSS REFERENCE TO RELATED APPLICATIONS

This application is a continuation-in-part of U.S. patent application Ser. No. 11/082,495 filed on Mar. 17, 2005 and entitled "Surgical Instrument Incorporating an Electrically Actuated Articulation Mechanism," pending which claims priority to U.S. Provisional Application No. 60/591,694 filed on Jul. 28, 2004 and entitled "Surgical Instrument Incorporating an Electrically Actuated Articulation Mechanism." These applications are hereby incorporated by reference in their entireties.

FIELD OF THE INVENTION

The present invention relates broadly to surgical devices, and in particular to methods and devices for articulating and actuating a surgical stapler using electrically expandable and contractible actuators, such as electroactive polymers.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that can articulate relative to the staple shaft, and that can be actuated to apply staples to tissue. Some linear end effectors simultaneously make a longitudinal incision in tissue and apply lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. Some current staplers also use reciprocating wedges which, when driven distally, pass through openings in the staple cartridge and engage drivers supporting the staples to effect the firing of the staples toward the anvil.

One drawback to current stapling devices is that a large force is required to effect articulation and actuation, and the force changes throughout the course of the firing stroke. Most current stapling devices utilize one or more hand-squeezed triggers. During articulation, the load is low when the end effector is close to linearly aligned with the shaft, and it increases as the end effector is articulated. During actuation, the load is low during early portions of the stroke when the staples are advancing out of the cartridge and piercing the tissue. Once the staples enter into the anvil pockets, the resistance and load rises rapidly as the staple legs buckle. Then the resistance and load drop down and rise again as the staples are formed. In contrast, the operator has maximum effective strength at the early and mid-stages of the firing stroke, whereas the effective strength is minimized during the final stages of closure. The large force necessary to effect articulation and actuation, as well as the variations in the force, can often exceed the surgeon's hand strength and could potentially result in binding or other malfunctions that may occur when an unexpectedly higher force is required.

The large force required to effect firing can also interfere with the flexibility or adjustability of the shaft. Currently, the end effector can be pivotally coupled to the shaft, or the shaft can be flexible to allow the shaft to travel through a curved pathway. The transfer of force from the handle to the end effector can necessarily interfere with the pivoted or curved orientation of the shaft, potentially causing it to straighten.

Accordingly, there remains a need for methods and devices for actuating and/or articulating a surgical stapler, and in particular for methods and devices that require a low force to effect actuation and/or articulation of a surgical stapler.

BRIEF SUMMARY OF THE INVENTION

The present invention generally provides methods and devices for actuating and/or articulating a surgical stapler. In one embodiment, a surgical stapler is provided having a stapling mechanism or end effector that is movably coupled to a distal end of an elongate shaft. An electrically expandable and contractible actuator, such as an electroactive polymer actuator, can be used to pivotally or angularly adjust a position of the stapling mechanism relative to the elongate shaft by delivering energy to the electroactive polymer actuator. In another embodiment, an electroactive polymer actuator can be used to actuate the staple applying assembly, thereby driving one or more staples, and preferably at least two linear rows of staples, into tissue. The actuator can alternatively or additionally drive a blade distally to cut tissue being stapled.

In one exemplary embodiment, the surgical stapler can include at least one electroactive polymer actuator coupled between an elongate shaft and a linear staple applying assembly, and the electroactive polymer actuator(s) can be adapted to selectively pivot the linear staple applying assembly relative to the elongate shaft when energy is delivered to at least one of the electroactive polymer actuators. The linear staple applying assembly can be movably coupled to the shaft using a variety of mating techniques. For example, the linear staple applying assembly can be coupled to the elongate shaft by a pivot joint. The elongate shaft can include a slide bar extending therethrough and having a distal end coupled to the pivot joint for moving the linear staple applying assembly.

While various techniques can be used to move the slide bar and effect pivotal movement of the staple applying assembly, in one exemplary embodiment the electroactive polymer actuator(s) can be configured to expand radially when energy is delivered thereto to move the slide bar laterally and thereby effect pivotal movement of the linear staple applying assembly. In an exemplary embodiment, the device includes a first electroactive polymer actuator disposed adjacent to a first side of the slide bar, and a second electroactive polymer actuator disposed adjacent to a second side of the slide bar. The first and second electroactive polymer actuators can be configured to expand radially when energy is delivered thereto to move the slide bar laterally. The slide bar can optionally include gears formed on a distal end thereof and adapted to engage corresponding gears formed in the pivot joint.

In another embodiment, the electroactive polymer actuator(s) can be configured to axially contract and radially expand. For example, the elongate shaft can include a first electroactive polymer actuator pivotally coupled to a first lateral side of the linear staple applying assembly, and a second electroactive polymer actuator coupled to a second opposed lateral side of the linear staple applying assembly. The first electroactive polymer actuator can axially contract when energy is delivered thereto to pivot the linear staple applying assembly in a first direction, and the second electroactive polymer actuator can axially contract when energy is delivered thereto to pivot the linear staple applying assembly in a second direction opposite to the first direction.

In another embodiment, the linear staple applying assembly can be movably coupled to the elongate shaft by a flexible portion. Several electroactive polymer actuators can be coupled to the flexible portion at distinct locations, and each of the electroactive polymer actuators can be configured to change orientations when energy is selectively delivered thereto to flex the flexible portion in a desired direction.

A method for stapling tissue is also provided and it can include inserting an elongate shaft of a surgical stapler into a body lumen to position a staple applying assembly movably coupled to a distal end of the elongate shaft adjacent to a surgical site, capturing tissue between opposed jaws of the staple applying assembly, delivering energy to at least one electroactive polymer actuator to pivot the staple applying assembly relative to the elongate shaft, and actuating the staple applying assembly to drive at least one linear row of staples from one of the jaws and into the tissue. In one exemplary embodiment, the elongate shaft can include a slide bar extending therethrough and having a distal end coupled to a pivot joint formed between the elongate shaft and the staple applying assembly. Energy delivery to at least one electroactive polymer actuator can be effective to radially expand the electroactive polymer actuator(s) to move the slide bar laterally and thereby effect pivotal movement of the staple applying assembly. The amount of energy delivered to the each electroactive polymer actuator can correspond to a degree of movement of the staple applying assembly. In another embodiment, the linear staple applying assembly can be movably coupled to the elongate shaft by a flexible portion. The electroactive polymer actuator can include a plurality of electroactive polymer actuators coupled to the flexible portion at distinct locations, and energy can be is selectively delivered to the plurality of electroactive polymer actuators to flex the flexible portion in a desired direction.

In yet another embodiment, a surgical stapler is provided having an elongate shaft with a linear staple applying assembly formed on a distal end thereof and adapted to receive tissue. The staple applying assembly is coupled to at least one electroactive polymer actuator that is configured to drive at least one linear row of staples into tissue when energy is delivered to the electroactive polymer actuator. In one exemplary embodiment, the staple applying assembly includes a stapling mechanism and an anvil opposed to the stapling mechanism. The stapling mechanism can include a plurality of drivers disposed therein and adapted to drive a plurality of staples from the stapling mechanism toward the anvil. The electroactive polymer actuator can be coupled to each of the plurality of drivers such that energy can be selectively delivered to at least one of the electroactive polymer actuators to move at least one of the drivers and thereby drive at least one staple into tissue. In another embodiment, a plurality of electroactive polymers can be disposed within the staple applying assembly, and each electroactive polymer can be effective to drive a linear row of staples into tissue when energy is delivered thereto. The electroactive polymers can be adapted to be individually actuated to drive a staple from the stapling mechanism toward the anvil.

In yet another embodiment, the surgical stapler can include a push rod slidably disposed within the elongate shaft and adapted to drive a plurality of staples from the stapling mechanism toward the anvil when the push rod is moved distally. The push rod can be coupled to an electroactive polymer actuator that is adapted to move the push rod distally when energy is delivered to the electroactive polymer actuator. In an exemplary embodiment, the electroactive polymer actuator coupled to the push rod is adapted to axially expand and radially contract when energy is delivered thereto to move the push rod distally.

A method for applying one or more surgical staples to tissue is also provided and can include capturing tissue between opposed first and second jaws, and delivering energy to an electroactive polymer actuator to drive at least one linear row of staples from the first jaw through the tissue and against an anvil formed on the second jaw. In one embodiment, one or more driver(s) can be movably disposed within the first jaw, and energy delivery to the electroactive polymer actuator can be effective to move the driver(s) within the first jaw to drive staples therethrough and against the anvil. In another embodiment, delivering energy to the electroactive polymer actuator can be effective to move a push rod distally to advance a plurality of staple drivers that drive at least one linear row of staples from the first jaw through the tissue and against an anvil formed on the second jaw. In other aspects, energy can be selectively delivered to a plurality of electroactive polymer actuators disposed within the first jaw to drive at least one linear row of staples from the first jaw through the tissue and against an anvil formed on the second jaw. In yet another embodiment, delivering energy to an electroactive polymer actuator can be effective to advance a blade distally to cut tissue being stapled.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1A:
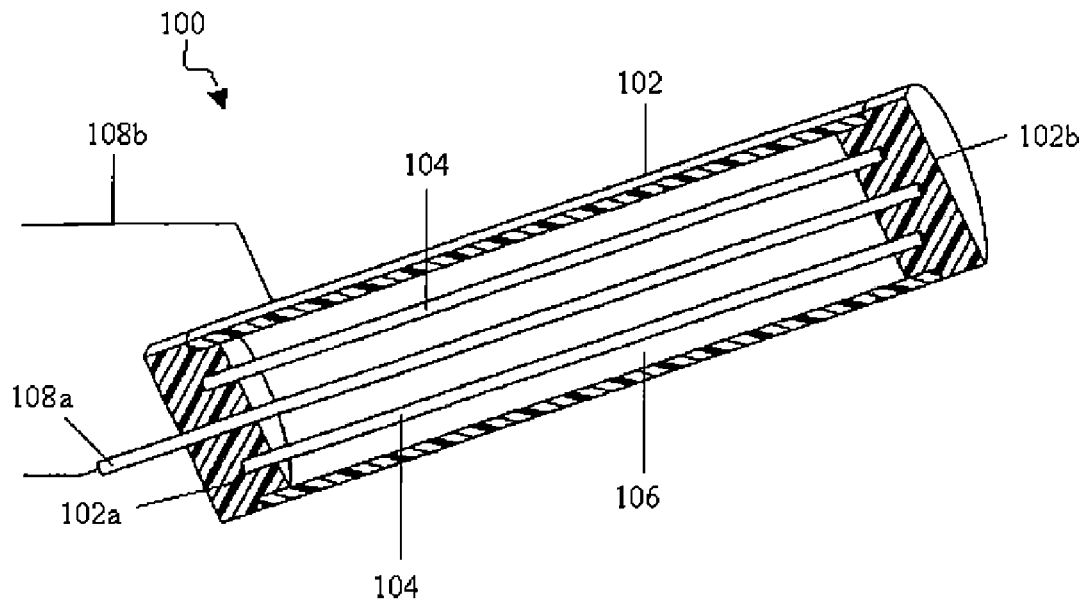
FIG. 1A is a cross-sectional view of a prior art fiber bundle type EAP actuator.

The present invention generally provides methods and devices for effecting movement of one or more components of a surgical stapler. In one exemplary embodiment, a surgical stapler is provided having a stapling mechanism or end effector that is movably coupled to a distal end of an elongate shaft. An electrically expandable and contractible actuator, such as an electroactive polymer actuator, can be used to pivotally or angularly adjust a position of the stapling mechanism relative to the elongate shaft by delivering energy to the electroactive polymer actuator. In another embodiment, an electroactive polymer actuator can be used to actuate the end effector, thereby driving one or more staples, and preferably at least two linear rows of staples, into tissue. The actuator can alternatively or additionally drive a blade distally to cut tissue being stapled. A person skilled in the art will appreciate that the surgical stapler can have a variety of configurations, and that the electroactive polymer actuator(s) can be coupled to one or more components of the surgical stapler to effect movement.

Electroactive Polymers

Electroactive polymers (EAPs), also referred to as artificial muscles, are materials that exhibit piezoelectric, pyroelectric, or electrostrictive properties in response to electrical or mechanical fields. In particular, EAPs are a set of conductive doped polymers that change shape when an electrical voltage is applied. The conductive polymer can be paired to some form of ionic fluid or gel and electrodes, and the flow of ions from the fluid/gel into or out of the conductive polymer can induce a shape change of the polymer. Typically, a voltage potential in the range of about 1V to 4 kV can be applied depending on the particular polymer and ionic fluid or gel used. It is important to note that EAPs do not change volume when energized, rather they merely expand in one direction and contract in a transverse direction.

One of the main advantages of EAPs is the possibility to electrically control and fine-tune their behavior and properties. EAPs can be deformed repetitively by applying external voltage across the EAP, and they can quickly recover their original configuration upon reversing the polarity of the applied voltage. Specific polymers can be selected to create different kinds of moving structures, including expanding, linear moving, and bending structures. The EAPs can also be paired to mechanical mechanisms, such as springs or flexible plates, to change the effect that is caused when voltage is applied.

There are two basic types of EAPs and multiple configurations for each type. The first type is a fiber bundle that can consist of numerous fibers bundled together to work in cooperation. The fibers typically have a size of about 30-50 microns. These fibers may be woven into the bundle much like textiles and they are often referred to as EAP yarn. In use, the mechanical configuration of the EAP determines the EAP actuator and its capabilities for motion. For example, the EAP may be formed into long stands and wrapped around a single central electrode. A flexible exterior outer sheath will form the other electrode for the actuator as well as contain the ionic fluid necessary for the function of the device. When voltage is applied thereto, the EAP will swell causing the strands to contract or shorten. The fibers can alternatively be configured to expand or lengthen. An example of a commercially available fiber EAP material is manufactured by Santa Fe Science and Technology and sold as PANION™ fiber and described in U.S. Pat. No. 6,667,825, which is hereby incorporated by reference in its entirety.

Figure 1B:
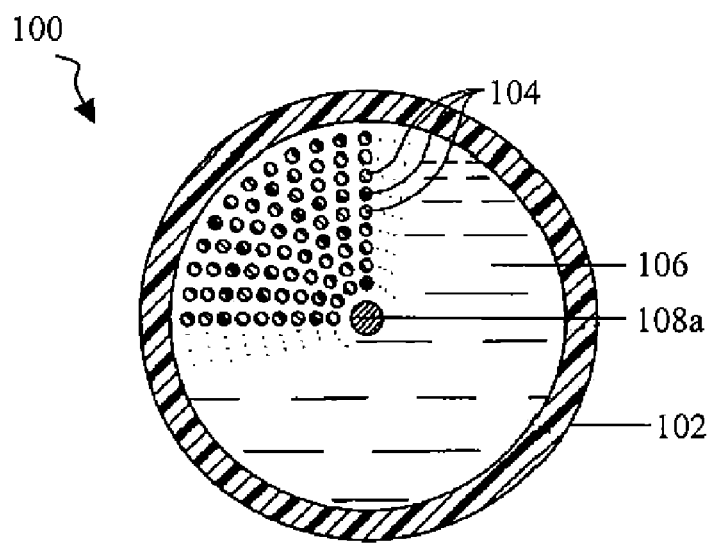
FIG. 1B is a radial cross-sectional view of the prior art actuator shown in FIG. 1A.

FIGS. 1A and 1B illustrate one exemplary embodiment of an EAP actuator 100 formed from a fiber bundle. As shown, the actuator 100 generally includes a flexible conductive outer sheath 102 that is in the form of an elongate cylindrical member having opposed end caps 102a, 102b formed thereon. The outer sheath 102 can, however, have a variety of other shapes and sizes depending on the intended use. As is further shown, the outer sheath 102 is coupled to an energy delivering electrode 108a and a return electrode 108b. In the illustrated embodiment, the energy delivering electrode 108a extends through one of the end caps, e.g., end cap 102a, through the inner lumen of the conductive outer sheath 102, and into the opposed end cap, e.g., end cap 102b. The energy delivering electrode 108a can be, for example, a platinum cathode wire, and it can be coupled to any portion of the outer sheath 102. The conductive outer sheath 102 can also include an ionic fluid or gel 106 disposed therein for transferring energy from the energy delivering electrode 108a to the EAP fibers 104, which are disposed within the outer sheath 102. In particular, several EAP fibers 104 are arranged in parallel and extend between and into each end cap 102a, 102b. As noted above, the fibers 104 can be arranged in various orientations to provide a desired outcome, e.g., radial expansion or contraction, or bending movement. In use, energy can be delivered to the actuator 100 through the active energy delivering electrode 106a. The energy will cause the ions in the ionic fluid to enter into the EAP fibers 104, thereby causing the fibers 104 to expand in one direction, e.g., radially such that an outer diameter of each fiber 104 increases, and to contract in a transverse direction, e.g., axially such that a length of the fibers decreases. As a result, the end caps 102a, 102b will be pulled toward one another, thereby contracting and decreasing the length of the flexible outer sheath 102.

The other type of EAP is a laminate structure, which consists of one or more layers of an EAP, a layer of ionic gel or fluid disposed between each layer of EAP, and one or more flexible plates attached to the structure. When a voltage is applied, the laminate structure expands in one direction and contracts in a transverse or perpendicular direction, thereby causing the flexible plate(s) coupled thereto to shorten or lengthen, or to bend or flex, depending on the configuration of the EAP relative to the flexible plate(s). An example of a commercially available laminate EAP material is manufactured by Artificial Muscle Inc, a division of SRI Laboratories. Plate EAP material, referred to as thin film EAP, is also available from EAMEX of Japan.

Figure 2A:
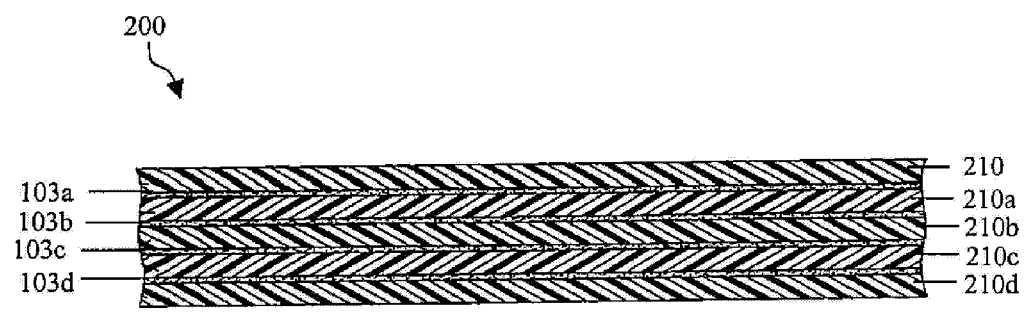
FIG. 2A is a cross-sectional view of a prior art laminate type EAP actuator having multiple EAP composite layers.
Figure 2B:
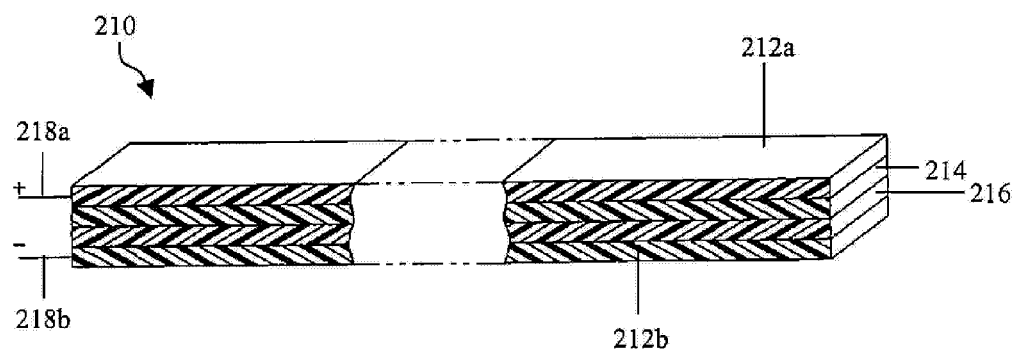
FIG. 2B is a perspective view of one of the composite layers of the prior art actuator shown in FIG. 2A.

FIGS. 2A and 2B illustrate an exemplary configuration of an EAP actuator 200 formed from a laminate. Referring first to FIG. 2A, the actuator 200 can include multiple layers, e.g., five layers 210, 210a, 210b, 210c, 210d are shown, of a laminate EAP composite that are affixed to one another by adhesive layers 103a, 103b, 103c, 103d disposed therebetween. One of the layers, i.e., layer 210, is shown in more detail in FIG. 2B, and as shown the layer 210 includes a first flexible conductive plate 212a, an EAP layer 214, an ionic gel layer 216, and a second flexible conductive plate 212b, all of which are attached to one another to form a laminate composite. The composite can also include an energy delivering electrode 218a and a return electrode 218b coupled to the flexible conductive plates 212a, 212b, as further shown in FIG. 2B. In use, energy can be delivered to the actuator 200 through the active energy delivering electrode 218a. The energy will cause the ions in the ionic gel layer 216 to enter into the EAP layer 214, thereby causing the layer 214 to expand in one direction and to contract in a transverse direction. As a result, the flexible plates 212a, 212b will be forced to flex or bend, or to otherwise change shape with the EAP layer 214.

Surgical Stapler

Figure 3:
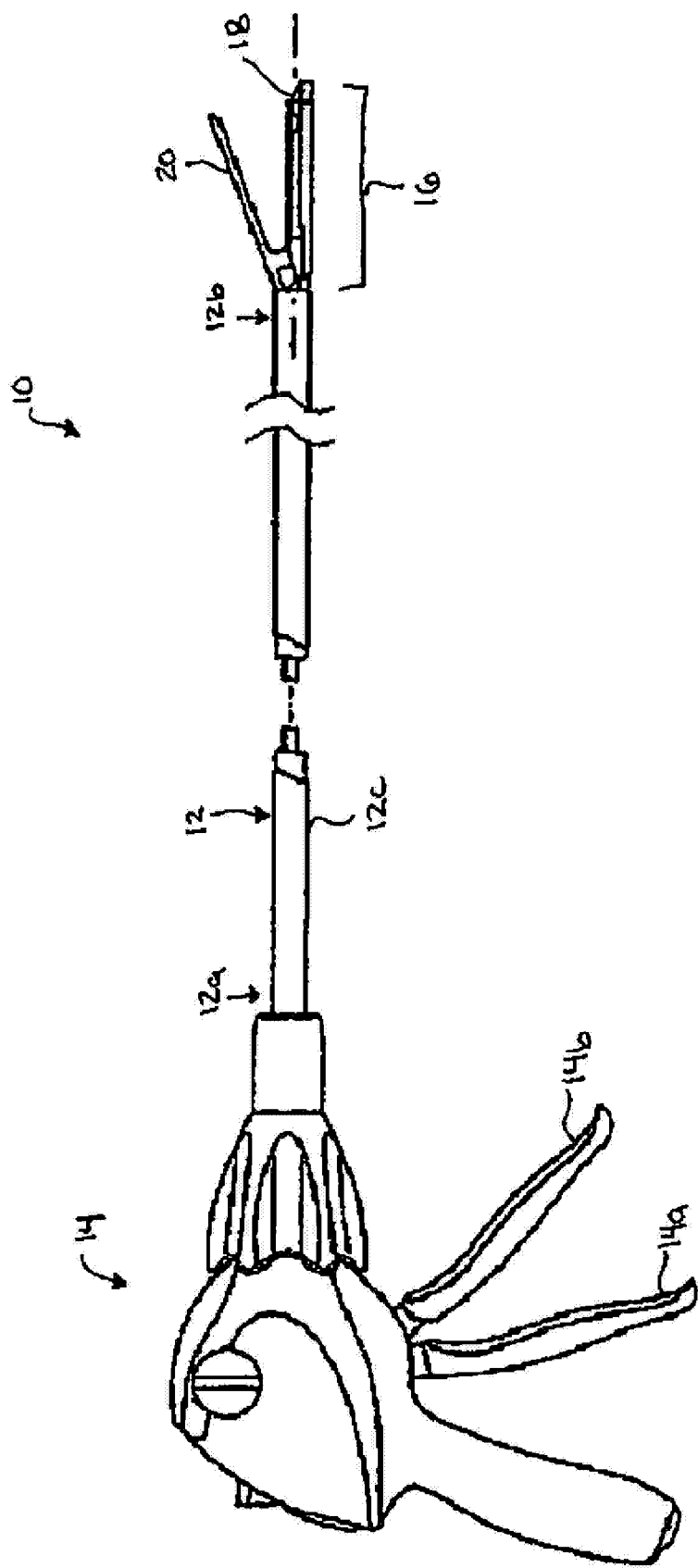
FIG. 3 is a side view of one exemplary embodiment of a surgical stapler having a handle, an elongate shaft, and an end effector coupled to a distal end of the elongate shaft.

As previously indicated, in an exemplary embodiment surgical stapling methods and devices are provided that utilize electrically expandable and contractible actuators, such as EAP actuators, to effect articulation and/or actuation of various components of the device. While the various embodiments are described as having EAP actuators for affecting articulation and/or actuation without mechanical assistance, the actuators can alternatively be configured to supplement mechanical articulation and/or actuation. For example, the EAP actuators can be used to reduce the force in closing an end effector on a surgical stapler, including firing the staples and optionally driving a knife or blade through the assembly to cut the stapled tissue. FIG. 3 illustrates one exemplary embodiment of a surgical stapler 10 that can include one or more EAP actuators for effecting articulation and/or actuation. As previously noted, the various methods and devices disclosed herein for effecting articulation and actuation can be incorporated into virtually any surgical stapler known in the art. The illustrated surgical stapler 10 can also include a variety of other features known in the art and not disclosed herein.

In general, the stapler 10 includes an elongate shaft 12 having a handle 14 coupled to a proximal end 12a thereof, and a staple applying assembly or end effector 16 coupled to a distal end 12b thereof. The end effector 16 includes opposed first and second jaws 18, 20 that are adapted to receive tissue therebetween. The first jaw 18 is adapted to contain a staple cartridge having multiple staples disposed therein and configured to be driven into tissue, and the second jaw 20 forms an anvil for deforming the staples. The handle 14 can include one or more triggers coupled thereto for articulating the end effector 16 relative to the elongate shaft 12, closing the end effector 16, and/or actuating (firing) the stapling apparatus. FIG. 3 illustrates a first trigger 14a movably coupled to the handle 14 for closing the opposed jaws 18, 20 of the end effector 16. Actuation of the first trigger 14a is effective to slide a closure tube 12c over the jaws 18, 20 to close the jaws 18, 20. The handle 14 also includes a second trigger 14b movably coupled thereto for firing the staple cartridge in the first jaw 20 to deliver one or more staples or clips into tissue. The second trigger 14b can also be effective to advance a blade distally through the staple cartridge in the first jaw 18 to cut stapled tissue. Exemplary techniques for firing staples and cutting tissue will be discussed in more detail below. While not shown, the handle 14 can additionally or alternatively include a trigger, rotatable knob, lever, sliding knob, or other mechanism for articulating the end effector 16 relative to the elongate shaft 16, closing the jaws, and actuating the end effector 16. In use, the surgical stapler 10 is particularly suitable for endoscopic and laparoscopic procedures, as the relative small diameter of the elongate shaft 12 allows it to fit through small access ports or pathways. The stapler, however, can be adapted for use in a variety of medical procedures.

Articulation

Figure 4A:
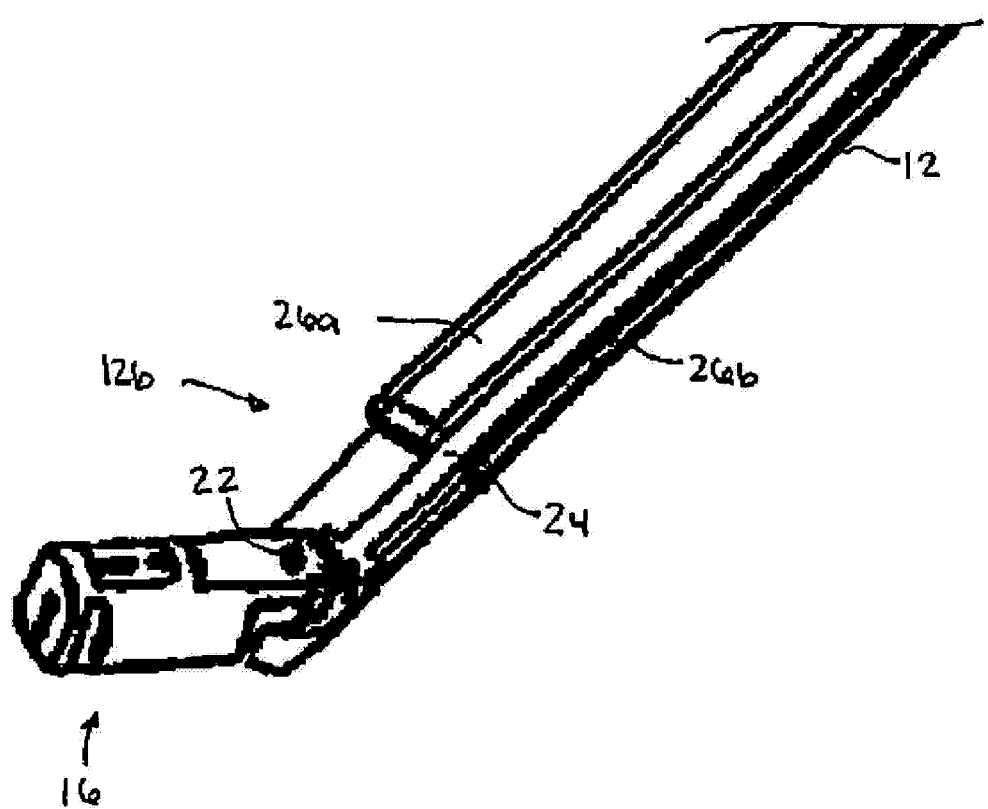
FIG. 4A is a partially cross-sectional view of the end effector shown in FIG. 3, showing EAP actuators for effecting articulation of the end effector.

FIGS. 4A-7 illustrate various exemplary embodiments of techniques for articulating the end effector 16 relative to the elongate shaft 12 to facilitate positioning of the end effector 16 adjacent to tissue to be stapled. Referring first to FIGS. 4A-4C, a distal end 12b of the elongate shaft 12 is shown coupled to a proximal end of the end effector 16 by a pivot joint 22, such that the end effector 16 can pivot relative to the shaft 12 about the pivot joint 22. The device 10 also includes a slide bar 24 extending through the elongate shaft and having a distal end 24d with gear teeth 24t formed thereon and adapted to engage corresponding gear teeth 16t formed on the end effector 16. The device 10 can also include one or more electrically expandable and contractible actuators, such as an EAP actuator, for moving the slide bar 24 to cause the gear teeth 24t on the slide bar 24 to move the gear teeth 16t on the end effector 16 and thereby pivot the end effector 16 relative to the elongate shaft 12. While the EAP actuator(s) can effect movement of the slide bar 24 using a variety of techniques, in one exemplary embodiment the EAP actuators are configured to move the slide bar 24 laterally. In particular, a first EAP actuator 26a can extend through at least a portion of the elongate shaft 12 adjacent to a first lateral side of the slide bar 24, and a second EAP actuator 26b can extend through at least a portion of the elongate shaft 12 adjacent to a second, opposed lateral side of the slide bar 24, as shown in FIGS. 4A-4C. Either type of EAP actuator can be used, but in an exemplary embodiment the EAP actuators 26a, 26b are laminate type EAP actuators that are adapted to expand laterally when energy is delivered thereto. FIGS. 4A and 4C illustrate the first EAP actuator 26a laterally expanded to move the slide bar 24 laterally toward the second EAP actuator 26b, thereby causing the slide bar 24 to pivot the end effector 16 in a direction opposite to the direction of movement of the slide bar 24. FIG. 4B illustrates both actuators 26a, 26b in a non-expanded, un-actuated configuration, where no energy is delivered to either actuator 26a, 26b. Energy can be delivered to the actuators 26a, 26b through electrodes extending through the shaft 12 and coupled to an energy source disposed within the handle 14 or coupled to the handle 12, e.g., via an electrical outlet or other energy source. The handle 14 can also include a control mechanism, such as a rotatable knob or dial, coupled thereto and adapted to control the amount of energy delivered to each actuator 26a, 26b. The amount of energy delivered to each actuator 26a, 26b is determinative of the amount of expansion of the actuators 26a, 26b, thus allowing the amount of pivotal movement of the end effector 16 to be selectively adjusted.

Figure 4B:
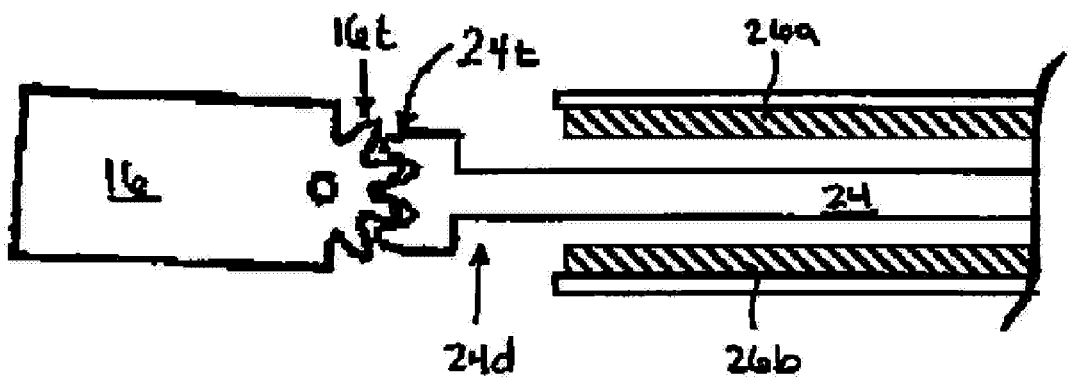
FIG. 4B is a cross-sectional view of the end effector shown in FIG. 4A, showing the EAP actuators in a non-actuated configuration.
Figure 4C:
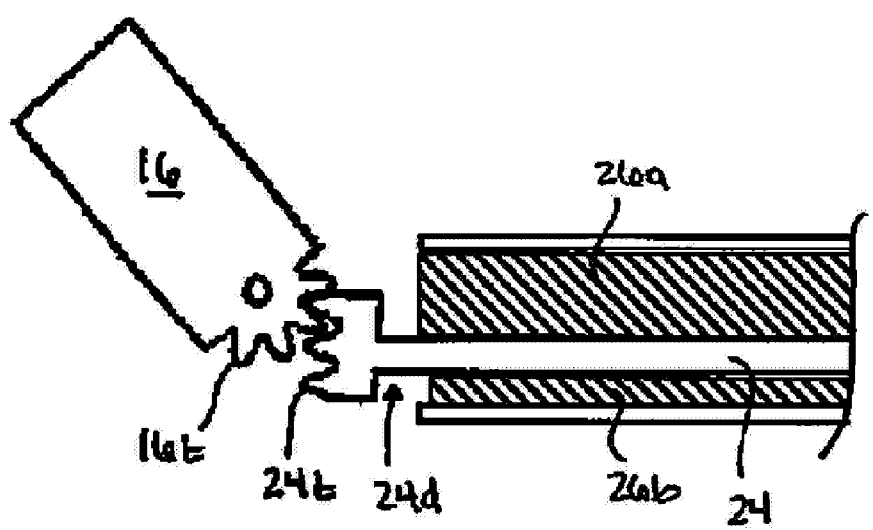
FIG. 4C is a cross-sectional view of the end effector shown in FIG. 4A, showing one of the EAP actuators electrically actuated to articulate the end effector.

A person skilled in the art will appreciate that, while FIGS. 4A-4C illustrate a laterally-moving slide bar 24 with laterally expanding EAP actuators 26a, 26b, the slide bar 24 and actuators 26a, 26b can have a variety of other configurations. For example, multiple EAP actuators in the form fiber bundles can extend laterally between an inner surface of the elongate shaft 12 and the slide bar 24. When energy is delivered to the actuators, the actuators can contract or shorten in length to pull the slide bar 24 toward the elongate shaft 12, thereby moving the slide bar 24 laterally. Alternatively, the slide bar 24 can be configured to move longitudinally to effect movement of the end effector 16, and the EAP actuator can be used to effect longitudinal movement of the slide bar 24. In other embodiments, the slide bar itself, or at least a portion of the slide bar, can be formed from an EAP actuator that is adapted to expand axially in a desired direction to move the slide bar laterally.

Figure 5A:
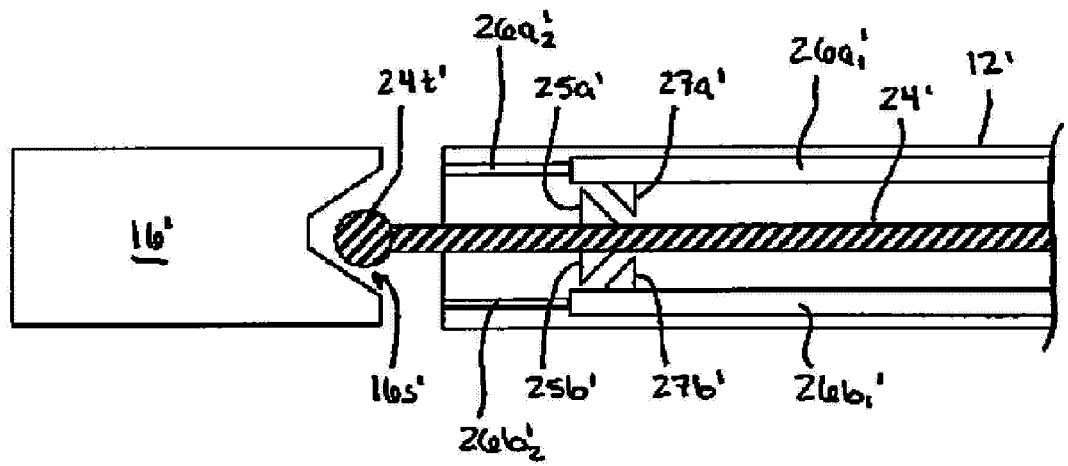
FIG. 5A is a partially cross-sectional view of another embodiment of an end effector movably coupled to a distal portion of an elongate shaft and having EAP actuators for articulating the end effector.
Figure 5B:
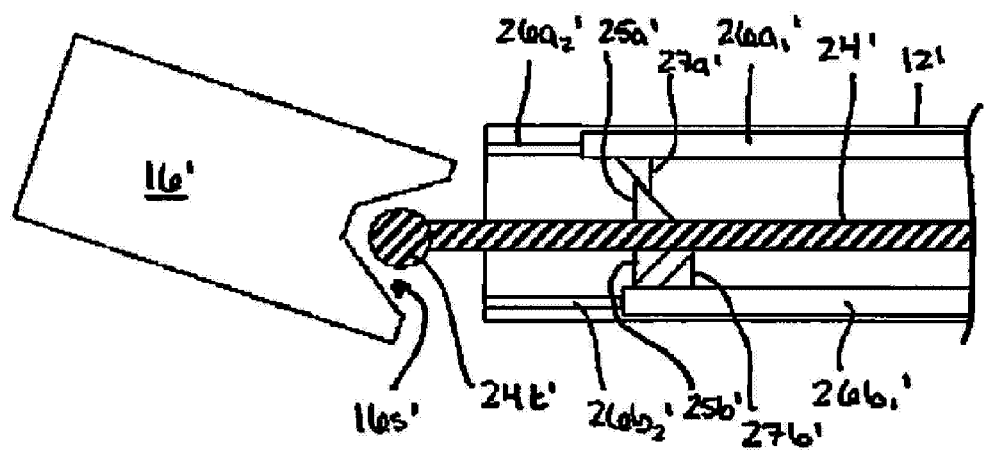
FIG. 5B is a partially cross-sectional view of the end effector and elongate shaft shown in FIG. 5A, showing one of the EAP actuators electrically actuated to articulate the end effector.

FIGS. 5A and 5B illustrate another embodiment of a technique for articulating an end effector 16' relative to an elongate shaft 12'. In this embodiment, the elongate shaft 12' includes a slide bar 24' extending therethrough and having a ball 24t' formed on a distal end thereof and received within a corresponding socket 16s' formed in a proximal end of the end effector 16'. The slide bar 24' also includes cam surfaces 25a', 25b' formed thereon, preferably at a location proximal to the distal end of the elongate shaft 12'. The cam surfaces 25a', 25b' can have a variety of shapes and sizes, but in an exemplary embodiment, as shown, the cam surfaces 25a', 25b' extend outward from opposed sides of the slide bar 24' and they are wedge-shaped members that increase in width in a proximal-to-distal direction. The device also includes first and second actuating members $26a_1'$, $26b_1'$ extending through the elongate shaft 12' and positioned on opposed sides of the slide bar 24'. Each actuating member $26a_1'$, $26b_1'$ includes a cam surface 27a', 27b' formed thereon and adapted to abut against the cam surfaces 25a', 25b' formed on the slide bar 24'. As a result, distal movement of the first actuating member 26a' will cause the cam surface 27a' formed thereon to slide against the cam surface 25a' formed on the slide bar 24', thereby moving the slide bar 24' laterally away from the first actuating member 26a'. As a result of the lateral movement of the slide bar 24', the ball 24t' will cause the end effector 16' to pivot relative to the elongate shaft 12'. Conversely, distal movement of the second actuating member 26b' will cause the cam surface 27b' formed thereon to slide against the cam surface 25b' formed on the slide bar 24', thereby moving the slide bar 24' laterally away from the second actuating member 26b', and thus pivoting the end effector 16' in an opposite direction. A biasing element (not shown), such as a spring, can be disposed on each side of the slide bar 24' to bias the slide bar 24' to the central, resting position shown in FIG. 5A, thereby allowing the slide bar 24' to return to the resting position when the actuating member 26a', 26b' is moving proximally.

In an exemplary embodiment, movement of each actuating member $26a_1'$, $26b_1'$ can be achieved using an EAP actuator coupled thereto. As shown in FIGS. 5A and 5B, an EAP actuator cord $26a_2'$, $26b_2'$, preferably in the form of a fiber bundle type actuator, extends between a distal end of each actuating member $26a_1'$, $26b_1'$ and a distal end of the shaft 12'. When energy is selectively delivered to one of the EAP actuating cords, e.g., the first actuating cord $26a_2'$, the cord $26a_2'$ will axially contract or shorten, as shown in FIG. 5B, thereby pulling the actuating member $26a_1'$ coupled to the actuated EAP cord $26a_2'$ in a distal direction. The cam surface 27a' on the actuating member $26a_1'$ will abut against the cam surface 25a' on the slide bar 24' to move the slide bar 24' laterally toward the second actuating member $26b_1'$. As a result, the ball 24t' on the distal end of the slide bar 24' will cause the end effector 16' to articulate or pivot thereabout.

A person skilled in the art will appreciate that the EAP actuators can have a variety of other configurations, and they can effect movement of the slide bar 24' using a variety of other techniques. For example, rather than pulling the slide bar 24' distally when energy is delivered to the EAP actuating cords $26a_2'$, $26b_2'$, the EAP actuators can be coupled to a proximal end of the slide bar 24' and they can be adapted to push the slide bar 24' distally. In other embodiments, the cam surface 27a', 27b' formed on each actuating member $26a_1'$, $26b_1'$ can be formed from an EAP actuator such that energy delivery to the cam surface 27a', 27b' causes the cam surface 27a', 27b' to expand toward the slide bar 24', thereby moving the slide bar 24' in a desired direction to articulate the staple applying apparatus 16'. The amount of movement of each actuating member $26a_1'$, $26b_1'$, and thus the amount of articulation of the staple applying apparatus 16', can also be controlled by controlling the amount of energy delivered to each EAP actuator.

Figure 6A:
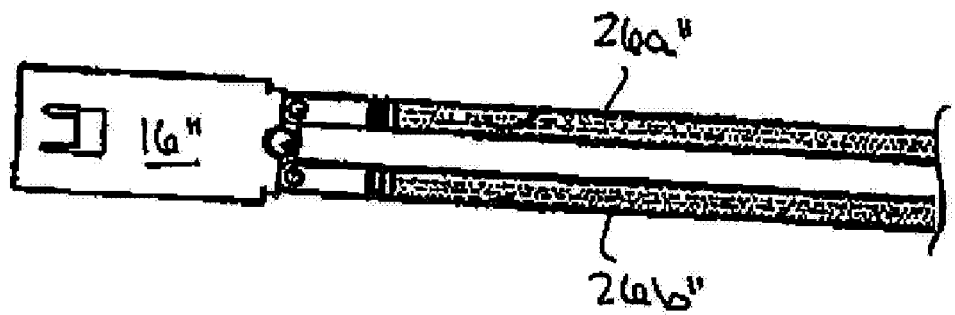
FIG. 6A is a partially cross-sectional view of yet another embodiment of an end effector movable coupled to a distal portion of an elongate shaft and having EAP actuators for articulating the end effector.
Figure 6B:
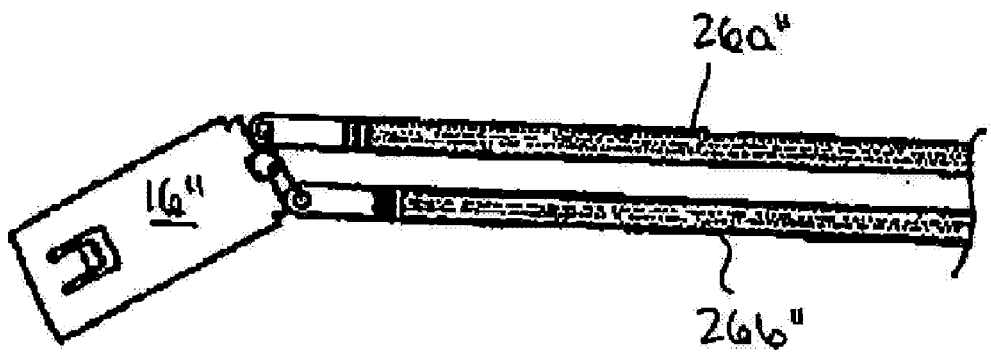
FIG. 6B is a partially cross-sectional view of the end effector and elongate shaft shown in FIG. 6A, showing one of the EAP actuators electrically actuated to articulate the end effector.

FIGS. 6A and 6B illustrate yet another embodiment of a technique for articulating an end effector 16". In this embodiment, rather than using a slide bar to pivot the end effector 16", two actuating members 26a", 26b" are coupled directly to opposed sides of the staple applying apparatus 16" to push and pull the staple applying apparatus 16" to effect articulation. In particular, a distal end of each actuating member 26a", 26b" is coupled to a proximal end of the staple applying apparatus 16" by a pivot joint, such that proximal movement of the first actuating member 26a" causes the staple applying apparatus 16" to pivot about the second actuating member 26b", and proximal movement of the second actuating member 26b" causes the staple applying apparatus 16" to pivot about the first actuating member 26a". The actuating members 26a", 26b" can be moved using a variety of techniques. For example, all or a portion of each actuating member 26a", 26b" can be formed from an EAP that is adapted to axially expand, or the actuating members 26a", 26b" can be coupled to an EAP actuator for moving the actuating members 26a", 26b" proximally and distally to articulate the end effector.

Figure 7:
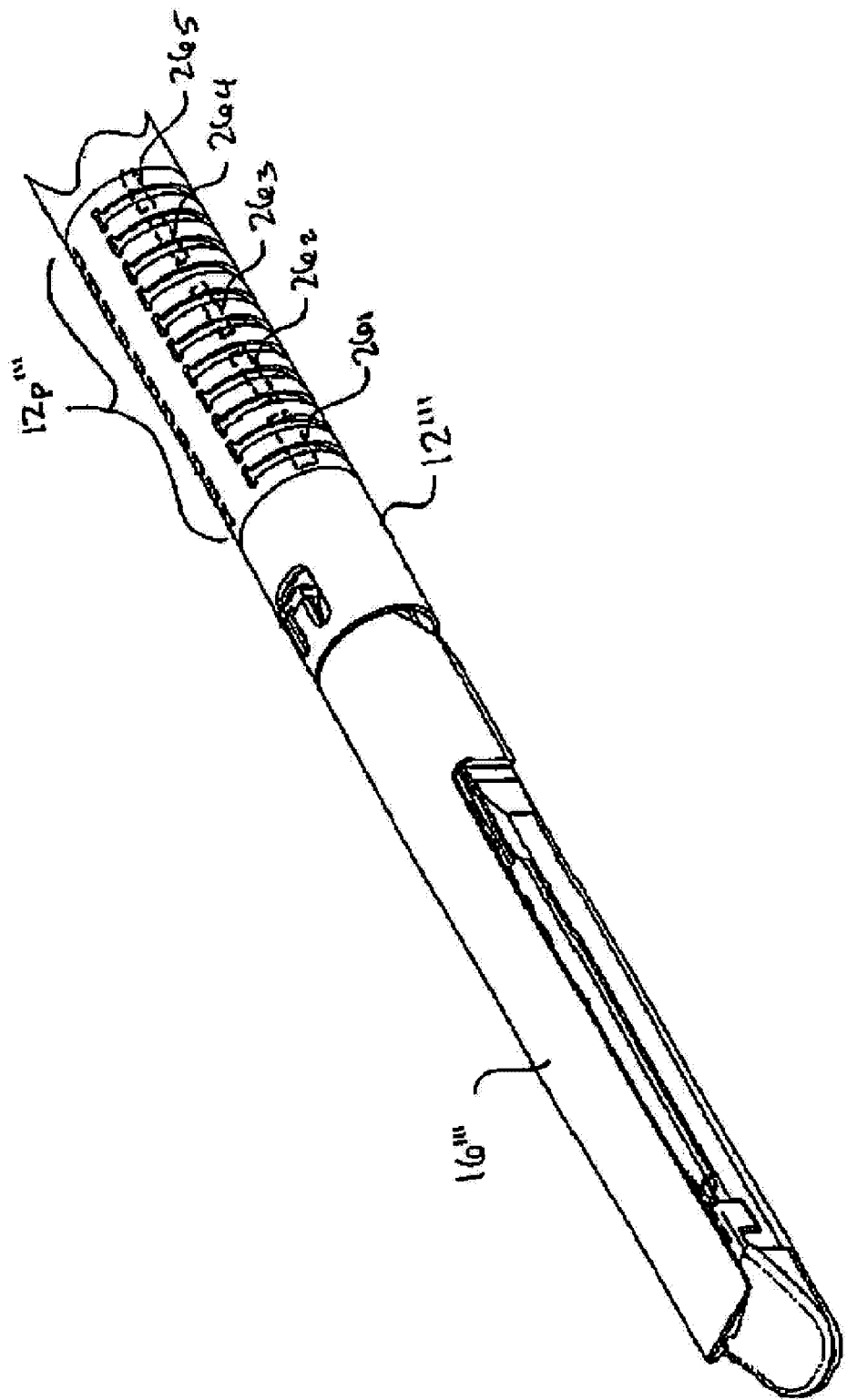
FIG. 7 is a perspective view of another embodiment of an end effector coupled to an elongate shaft having a flexible portion for articulating the end effector, and having multiple EAP actuators for flexing the flexible portion.

FIG. 7 illustrates yet another embodiment of a technique for articulating an end effector 16'''. In this embodiment, the elongate shaft 12''' includes a flexible portion 12p''' that is adapted to allow the end effector 16''' to articulate relative to the shaft 12'''. One or more EAP actuators can be positioned within, on, or around the flexible portion 12p''' of the elongate shaft 12''' at various locations, and the EAP actuators can be configured to flex the flexible portion 12p''' when energy is delivered to the actuators, thereby articulating the end effector 16'''. FIG. 7 illustrates multiple EAP actuators $26_1$, $26_2$, $26_3$, $26_4$, $26_5$ extending axially along distinct portions of the flexible portion 12p''' of the elongate shaft 12'''. While not shown, multiple EAP actuators can be positioned at various other locations around the circumference of the flexible portion 12p'''. In use, energy delivery to the first actuator $26_1$, for example, can cause the first actuator $26_1$ to axially contract thereby bending the a portion of the flexible portion 12p'''. A user can thus selectively deliver energy to one or more actuators to articulate and position the end effector 16''' as desired.

A person skilled in the art will appreciate that the EAP actuators can be incorporated into a variety of other articulation mechanisms to effect articulation of the end effector. By way of non-limiting example, U.S. patent application Ser. No. 10/061,908, entitled "Surgical Instrument Incorporating A Fluid Transfer Controlled Articulation Mechanism" and filed on Feb. 18, 2005, which is hereby incorporated by reference in its entirety, discloses a variety of articulation mechanisms that utilize fluid bladders to effect articulation of a surgical stapling assembly. Rather than using a fluid bladder, an EAP actuator can be used to apply a force to the device to effect articulation.

Actuation

As previously indicated, the present invention also provides exemplary methods and devices for actuating an end effector on a surgical stapler, including firing the staples and optionally driving a knife or blade through the assembly to cut the stapled tissue. FIGS. 8A-10B illustrate various exemplary embodiments of techniques for firing an end effector 16 and for driving a blade through the end effector to cut stapled tissue using one or more EAP actuators. A person skilled in the art will appreciate that the end effector can have a variety of configurations, and that EAP actuators can be incorporated into a variety of other end effectors to effect firing and/or cutting.

Figure 8A:
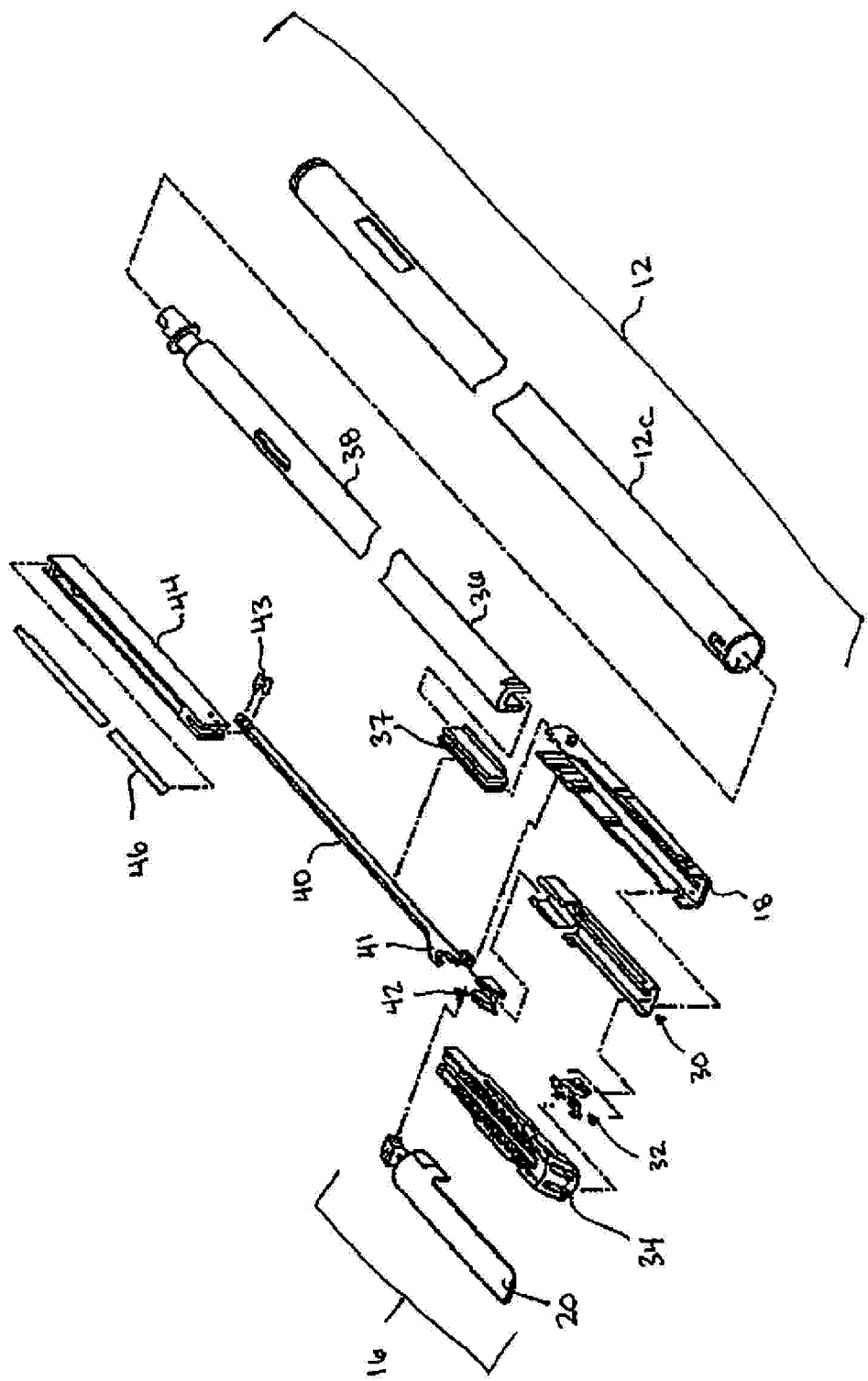
FIG. 8A is an exploded perspective view showing various components of the end effector and elongate shaft of the surgical stapler shown in FIG. 3.
Figure 8B:
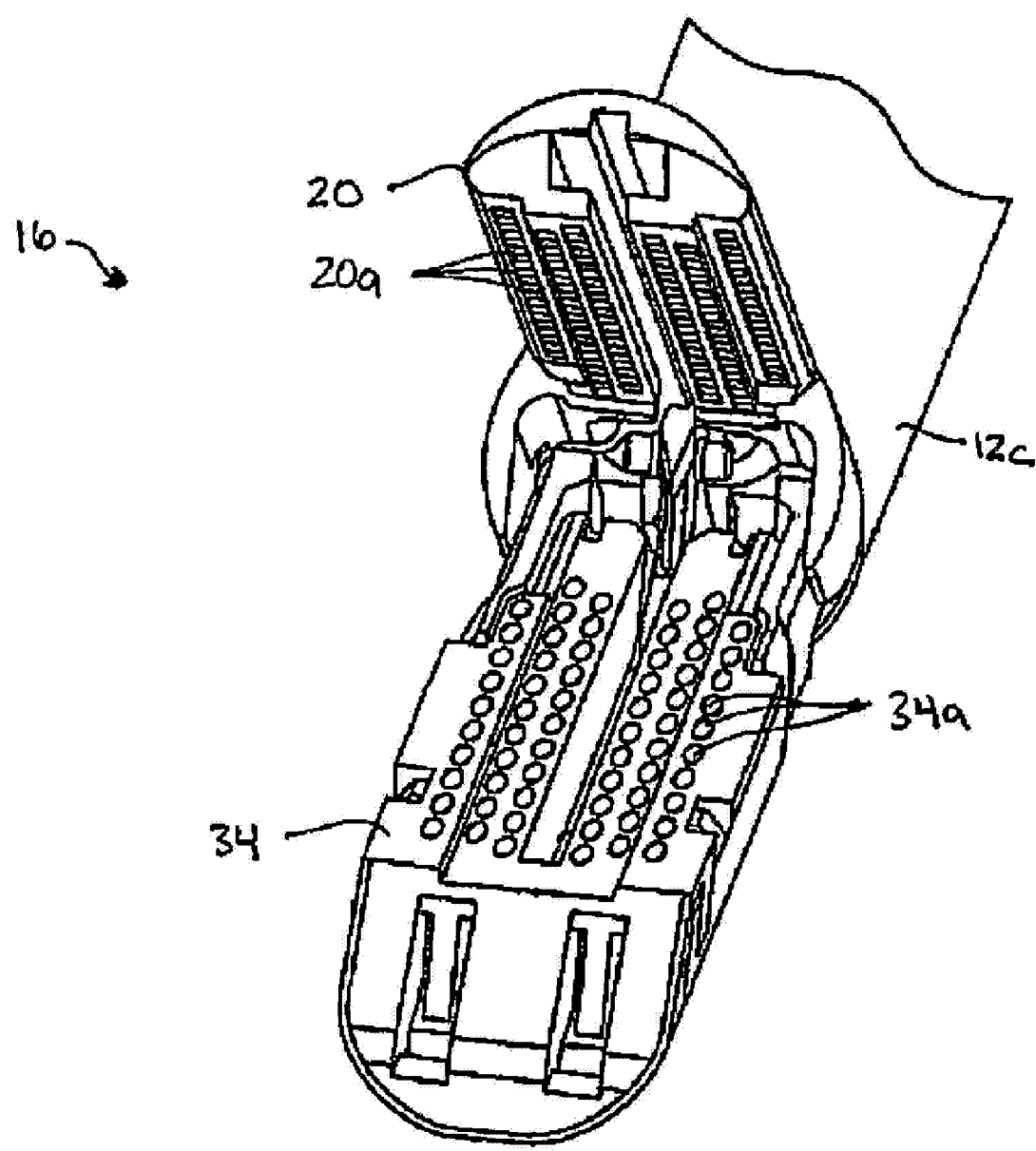
FIG. 8B is an end perspective view of the end effector of FIG. 3, showing opposed jaws in an open position.

FIGS. 8A-8D illustrate one exemplary embodiment of a technique for firing staples and cutting tissue using an EAP actuator. In this embodiment, an EAP actuator is used to longitudinally drive an assembly through the elongate shaft to drive a plurality of staple drivers disposed within a staple cartridge, and to cut tissue being stapled. FIG. 8A illustrates a distal portion of the surgical stapling device 10 of FIG. 3 in more detail, showing some of the components that form the elongate shaft 12 and the end effector 16. As previously discussed, the end effector 16 includes first and second opposed jaws 18, 20, which are shown in the open position in FIG. 8B. The first jaw 18 houses a tray 30 that holds a staple cartridge 34. The staple cartridge 34 is adapted to contain staples 33, preferably oriented in longitudinally-extending rows, as well as staple drivers 32, which are also preferably oriented in longitudinally-extending rows. The drivers 32 are effective to drive the staples 33 through openings 34a formed in the staple cartridge 34. In particular, as shown in more detail in FIG. 8C, movement of the drivers 32 toward the second jaw 20 will advance the staples 33 through the openings 34a formed in the staple cartridge 34 and toward corresponding grooves 20a formed in the second jaw 20, which forms the anvil.

The drivers 32 can be moved using a variety of techniques, but in the illustrated embodiment the drivers 32 are moved by advancing a wedge sled driver 42 through a longitudinally-extending slot formed in the staple cartridge 34. The wedge sled driver 42 can include camming surfaces that contact and lift the staple drivers 32 upward, driving the staples 33 up through openings 34a formed in the staple cartridge 34 and into the corresponding grooves 20a formed in the second jaw 20. In an exemplary embodiment, the wedge sled driver 42 can be moved using a push rod 40 that is slidably disposed through the elongate shaft 12 and that includes a distal end 41 that engages the wedge sled driver 42 to slide the wedge sled driver 42 relative to the staple cartridge 34. The distal end 41 of the push rod 40 can also include a cutting surface 41a formed thereon for cutting tissue during or after the tissue is stapled.

Figure 8C:
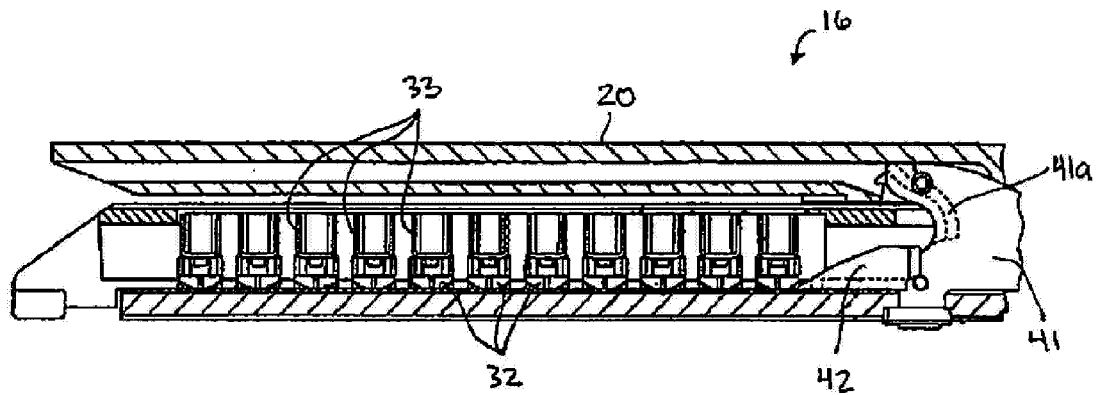
FIG. 8C is a side cross-sectional view of the end effector shown in FIG. 8B showing a cutting blade in a proximal position.
Figure 8D:
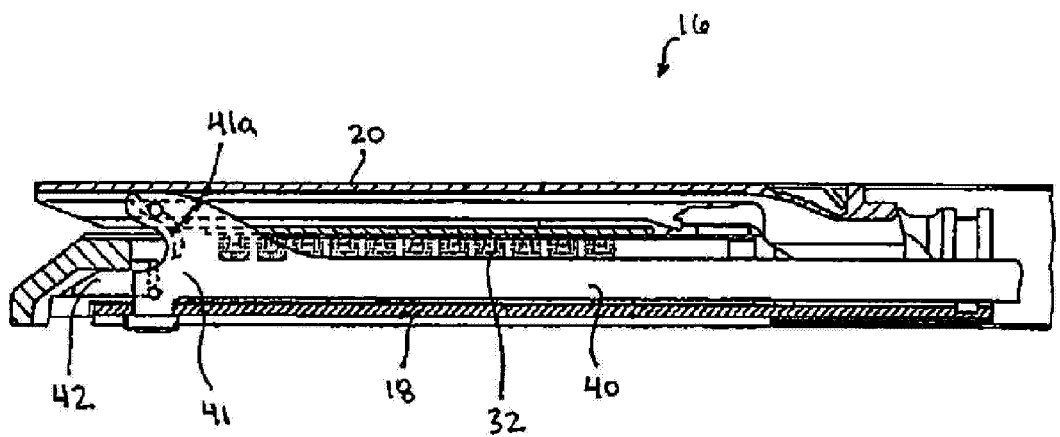
FIG. 8D is a side cross-sectional view of the end effector shown in FIG. 8C showing the cutting blade in a distal position.

In one exemplary embodiment, the push rod 40 can be advanced through the elongate shaft 12 of the device 10 using an EAP actuator. As shown in FIG. 8A, the proximal end of the push rod 40 is configured to couple to a firing trough 44. An EAP actuator 46 extends through the firing trough 44 and mates to the firing trough 44 at its distal end. A proximal end of the EAP actuator 46 can couple to a portion of the housing 14, and an electrode can be used to deliver energy to the EAP actuator 46 from an energy source disposed within or coupled to the housing 14. When energy is delivered to the EAP actuator 46, the actuator can axially expand to move the firing trough 44 and push rod 40 from an initial position, as shown in FIG. 8C, to a distal-most position, as shown in FIG. 8D. When the firing trough 44 and push rod 40 are moved distally, the wedge sled driver 42 drives the staple drivers 32 disposed within the staple cartridge 34 toward the second jaw 20, thereby driving the staples 33 through tissue engaged between the first and second jaws 18, 20. When energy delivery is terminated, the EAP actuator 46 will return to its unexpanded state, thereby moving the push rod 40 and firing trough 44 proximally to their initial position, and allowing the drivers 32 to return to their initial, un-actuated position. As is further shown in FIG. 8A, a portion of the push rod 40 can extend through a guide 37 that is effective to maintain alignment of the push rod 40 with the staple cartridge 34. A frame 36 can also be disposed around the push rod 40 and firing trough 44, and the entire assembly can move longitudinally within the closure tube 12c of the elongate shaft 12.

In one embodiment, energy delivery to the EAP actuator 46 can be controlled using the second trigger 14b that is movably coupled to the housing. The second trigger 14b can be coupled to an energy source, such as a battery disposed within the housing 14, an external battery pack, or an electrical outlet. Actuation of the second trigger 14b can be effective to increase the amount of energy delivered from the energy source, through an electrode, and to the EAP actuator 46, there moving the firing trough 44 and push rod 40. The amount of energy delivered can correspond to the amount of movement of the firing trough 44 and push rod 30. Alternatively, rather than using a pivoting trigger 14b, the handle 14 can include a button, lever, knob, dial, or other mechanism to control energy delivery to the EAP actuator 46. A person skilled in the art will appreciate that a variety of techniques can be used to control energy delivery to the EAP actuator 46.

While FIGS. 8A-8D illustrate an EAP actuator 46 that drives the firing trough 44 and the push rod 40 distally, the EAP actuator can have a variety of other configurations to move the wedge sled driver 42 through the staple cartridge 34. For example, in another embodiment the EAP actuator can be configured to axially contract or shorten, rather than axially expand or lengthen. As such, the EAP actuator can be coupled to the firing trough 44 or the push rod 40 in such a manner that will allow the EAP actuator to pull the firing trough 44 and push rod 40 distally as the EAP actuator axially contracts. In another embodiment, the EAP actuator 46 can replace the firing trough 44 and it can be directly connected to the push rod 40 to move the push rod 40 through the elongate shaft 12. Alternatively, a portion of the push rod 40 can be formed from an EAP actuator for directly moving the push rod 40, or the EAP actuator can replace the entire push rod 40, directly driving the wedge sled driver 42 through the staple cartridge 34.

Figure 9A:
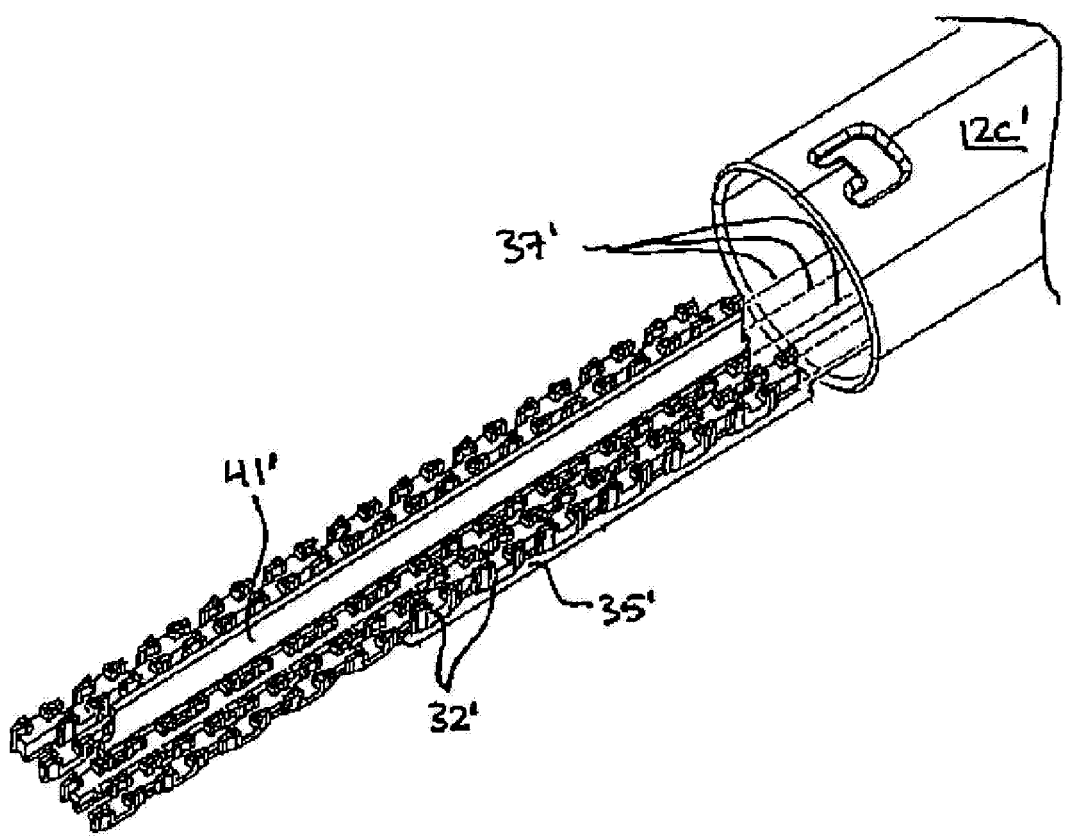
FIG. 9A is a top perspective view of a portion of another embodiment of an end effector having driver elements for driving staples and EAP actuators strips for driving the driver elements.
Figure 9B:
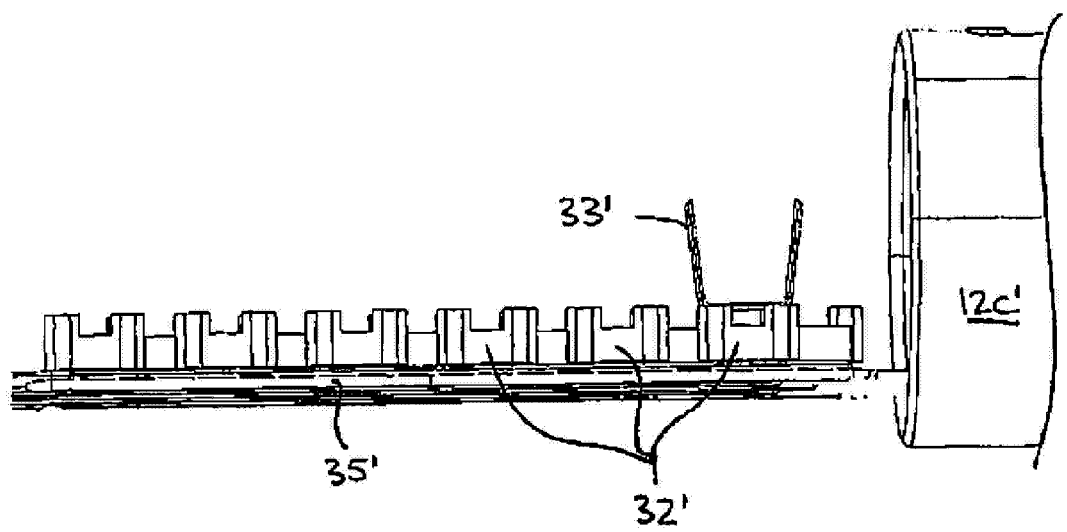
FIG. 9B is a side view of the end effector shown in FIG. 9A showing one of the EAP actuator strips positioned to drive several driver elements.

In another embodiment, rather than using a wedge sled drive 42 to move the drivers 32, multiple EAP actuator strips can be used to directly drive a plurality of staple drivers disposed within a staple cartridge. One such exemplary embodiment is illustrated in FIGS. 9A-9B, which show a portion of a closure tube 12c' and a portion of a staple cartridge. As shown, the staple cartridge includes multiple longitudinally-extending rows of drivers 32'. Each row of drivers 32' can include one or more EAP actuator strips 35' disposed there under and adapted to expand or increase in height when energy is delivered thereto to move the drivers 32' toward the anvil or second jaw 20. In an exemplary embodiment, the EAP actuator strips 35' are of the laminate type. The quantity of EAP actuator strips 35', and the number of drivers 32' driven by each EAP actuator strip 35', can vary. In the embodiment shown in FIGS. 9A and 9B, the staple cartridge (not shown) includes six longitudinally-extending rows of staple drivers 32', with eleven drivers 32' in each row. A single EAP actuator 35' can be disposed under each driver 32', or one or more elongate EAP actuator strip 35' can be disposed under several drivers 32'. FIGS. 9A and 9B illustrate a longitudinally-oriented EAP actuator strip 35' disposed under six drivers 32' in a first row of drivers. When energy is delivered to the EAP actuator strip 35', the EAP actuator strip 35' expands to move the drivers 32' disposed thereon toward the second jaw (not shown). The drivers 32' thus drive staples 33' disposed thereon into the recesses formed in the second jaw, to thereby staple tissue disposed between the jaws. Energy can be delivered to each actuator strip 35' through an electrode 37' that is coupled thereto and that is coupled to a power source.

As is further shown in FIGS. 9A and 9B, the device can also include a cutting blade 41' positioned between the rows of staple drivers 32'. The cutting blade 41' can be configured to move up and down between a retracted position wherein the cutting blade 41' is retracted into the staple cartridge, and an extended position, as shown, wherein the cutting blade 41' is extended toward the second jaw (not shown). A longitudinally-oriented EAP actuator strip (not shown) can be disposed under the cutting blade 41', and it can be adapted to expand or increase in height when energy is delivered thereto to move the cutting blade 41' from the retracted position to the extended position, thereby cutting tissue engaged between the jaws. Termination of energy delivery to the EAP actuator will return the cutting blade 41' to its retracted position.

Figure 10A:
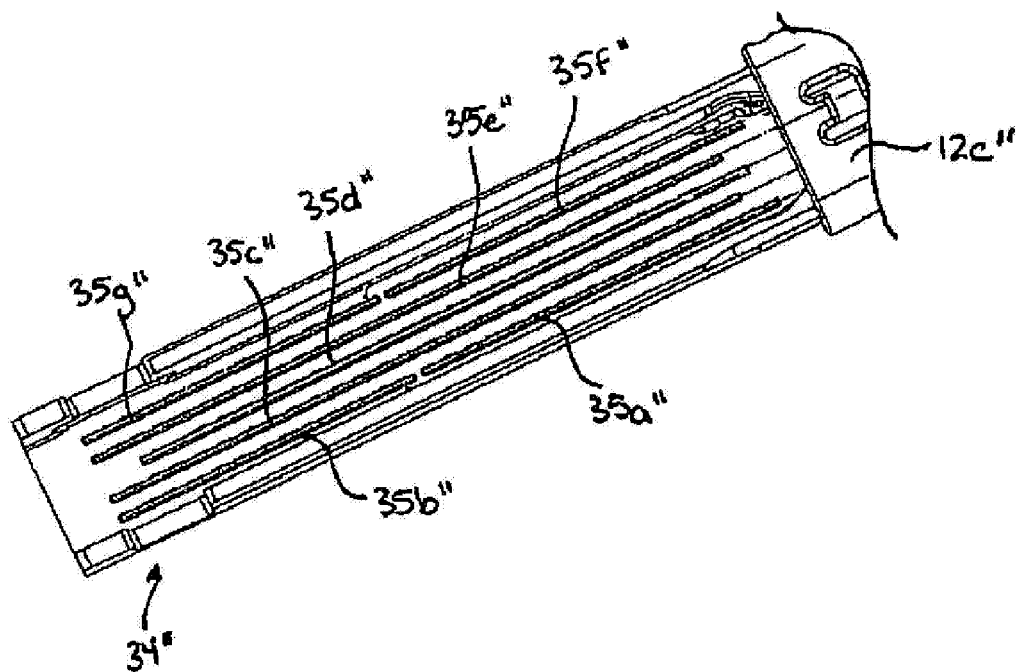
FIG. 10A is a top perspective view of another embodiment of an end effector for use with a surgical stapler, showing EAP drivers for directly driving staples.
Figure 10B:
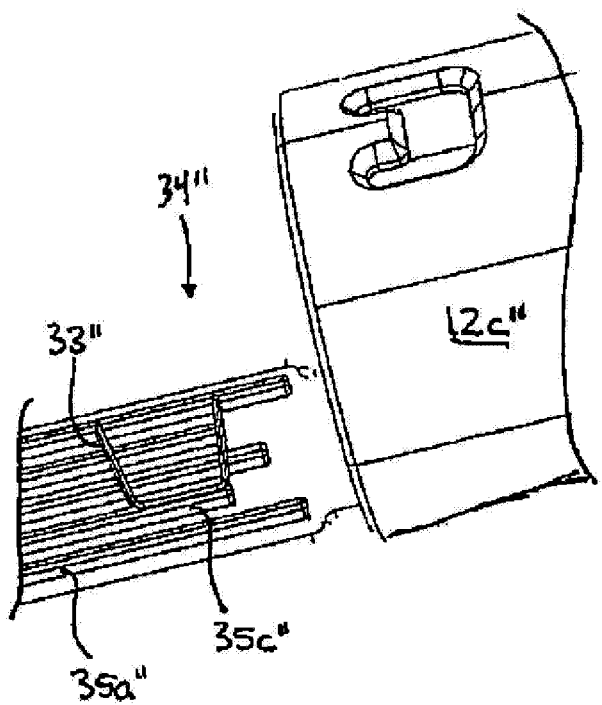
FIG. 10B is a top perspective view of a portion of the end effector shown in FIG. 10A, showing a staple positioned on one of the FAP drivers.

FIGS. 10A-10B illustrate yet another embodiment of a technique for firing staples using an EAP actuator. In this embodiment, multiple EAP actuators are used to directly drive a plurality of staples disposed within a staple cartridge. As shown, the staple cartridge 34", which is coupled to a distal end of the closure tube 12*c*", includes multiple elongate EAP actuator strips 35*a-g*" disposed therein. The actuator strips 35*a-g*" are arranged to directly drive staples 33" through the staple cartridge 34" and toward the second jaw, which forms the anvil. Multiple actuator strips 35*a-g*" can be used as they allow groups or zones of staples 33" to be separately driven into tissue. A person skilled in the art will appreciate that the EAP actuators 35*a-g*" can each be configured to individually drive a single staple or any number of staples. In use, when energy is delivered to the actuators 35*a-g*", e.g., via electrodes, the actuators 35*a-g*" expand toward the second jaw to drive the staples 33" toward the second jaw. When energy delivery is terminated, the actuators 35*a-g*" contract to return to an unexpanded state.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical stapler, comprising:
   an elongate shaft defining a longitudinal axis;
   a linear staple applying assembly movably coupled to the elongate shaft and adapted to deliver a plurality of staples; and
   an electroactive polymer actuator coupled between the elongate shaft and the linear staple applying assembly and adapted to selectively pivot the linear staple applying assembly relative to the elongate shaft when energy is delivered to the electroactive polymer actuator.

2. The surgical stapler of claim 1, wherein the linear staple applying assembly is movably coupled to the elongate shaft by a pivot joint.

3. The surgical stapler of claim 2, wherein the elongate shaft includes a slide bar extending therethrough and having a distal end coupled to the pivot joint, the electroactive polymer actuator being configured to move the slide bar laterally and thereby effect pivotal movement of the linear staple applying assembly.

4. The surgical stapler of claim 3, wherein the electroactive polymer actuator comprises a first electroactive polymer actuator disposed adjacent to a first side of the slide bar, and a second electroactive polymer actuator disposed adjacent to a second side of the slide bar, the first and second electroactive polymer actuators being configured to expand laterally when energy is delivered thereto to move the slide bar laterally.

5. The surgical stapler of claim 3, wherein the slide bar includes gears formed on a distal end thereof and adapted to engage corresponding gears formed in the pivot joint.

6. The surgical stapler of claim 1, wherein the electroactive polymer actuator comprises a first electro active polymer actuator extending between a first side of the elongate shaft and a first side of the linear staple applying assembly, and a second electroactive polymer actuator extending between a second opposed side of the elongate shaft and a second opposed side of the linear staple applying assembly.

7. The surgical stapler of claim 6, wherein the first and second electroactive polymer actuators are adapted to axially contract to pivot the linear staple applying assembly relative to the elongate shaft.

8. The surgical stapler of claim 1, wherein the linear staple applying assembly is movably coupled to the elongate shaft by a flexible portion.

9. The surgical stapler of claim 8, wherein the electroactive polymer actuator comprises a plurality of electroactive polymer actuators coupled to the flexible portion at distinct locations, each of the plurality of electroactive polymer actuators being configured to change orientations when energy is selectively delivered thereto to flex the flexible portion.

10. The surgical stapler of claim 1, further comprising a handle formed on a proximal end of the elongate shaft and having a control mechanism formed thereon for delivering energy to the at least one electroactive polymer actuator.

11. A surgical stapler, comprising:
    an elongate shaft having a linear staple applying assembly movably coupled to a distal end thereof, the staple applying assembly being in communication with an electroactive polymer actuator that is configured to angularly adjust a position of the staple applying assembly relative to the elongate shaft when energy is delivered to the electroactive polymer actuator.

12. The surgical stapler of claim 11, wherein the electroactive polymer actuator is adapted to axially expand and radially contract when energy is delivered thereto to angularly adjust a position of the staple applying assembly relative to the elongate shaft.

13. The surgical stapler of claim 12, wherein the elongate shaft includes a slide bar disposed therein and coupled to a pivot joint formed between the staple applying assembly and the elongate shaft, the electroactive polymer actuator being adapted to move the slide bar laterally to angularly adjust a position of the staple applying assembly relative to the elongate shaft when energy is delivered to the electroactive polymer actuator.

14. The surgical stapler of claim 11, wherein the electroactive polymer actuator is adapted to radially expand and axially contract when energy is delivered thereto to angularly adjust a position of the staple applying assembly relative to the elongate shaft.

15. The surgical stapler of claim 14, wherein the electroactive polymer actuator comprises a first electroactive polymer actuator coupled to a first side of the staple applying assembly and adapted to pivot the staple applying assembly in a first direction when energy is delivered to the first electroactive polymer actuator, and a second electroactive polymer actuator coupled to a second, opposed side of the staple applying assembly and adapted to pivot the staple applying assembly in a second, opposed direction when energy is delivered to the second electroactive polymer actuator.

16. A method for stapling tissue, comprising:
   inserting an elongate shaft of a surgical stapler into a body lumen to position a staple applying assembly movably coupled to a distal end of the elongate shaft adjacent to a surgical site;
   capturing tissue between opposed jaws of the staple applying assembly;
   delivering energy to an electroactive polymer actuator to pivot the staple applying assembly relative to the elongate shaft; and
   actuating the staple applying assembly to drive at least one linear row of staples from one of the jaws and into the tissue.

17. The method of claim 16, wherein the elongate shaft includes a slide bar extending therethrough and having a distal end coupled to a pivot joint formed between the elongate shaft and the staple applying assembly, and wherein delivering energy to the electroactive polymer actuator radially expands the electroactive polymer actuator to move the slide bar laterally and thereby effect pivotal movement of the staple applying assembly.

18. The method of claim 16, wherein the elongate shaft includes a slide bar extending therethrough and having a distal end coupled to a pivot joint formed between the elongate shaft and the staple applying assembly, and wherein delivering energy to the electroactive polymer actuator axially expands the electroactive polymer actuator to move the slide bar axially and thereby effect pivotal movement of the staple applying assembly.

19. The method of claim 16, wherein energy delivered to a first electroactive polymer actuator moves the staple applying assembly in a first direction, and energy delivered to a second electroactive polymer actuator moves the staple applying assembly in a second, opposed direction.

20. The method of claim 16, wherein an amount of energy delivered to the electroactive polymer actuator causes the staple applying assembly to move a corresponding amount.

21. The method of claim 16, wherein the linear staple applying assembly is movably coupled to the elongate shaft by a flexible portion, and wherein delivering energy selectively to the plurality of electroactive polymer actuators flexes the flexible portion.

22. The method of claim 16, wherein the electroactive polymer actuator comprises a plurality of electroactive polymer actuators coupled to the flexible portion at distinct locations, and wherein delivering energy selectively to the plurality of electroactive polymer actuators flexes the flexible portion in a desired direction.

* * * * *